US011986547B2

(12) United States Patent
Dimitrova et al.

(10) Patent No.: US 11,986,547 B2
(45) Date of Patent: *May 21, 2024

(54) COSMETIC COMPOSITION COMPRISING SILICONE MATERIALS

(71) Applicant: DOW SILICONES CORPORATION, Midland, MI (US)

(72) Inventors: Tatiana Dimitrova, Seneffe (BE); Charlene Fournier, Seneffe (BE)

(73) Assignee: DOW SILICONES CORPORATION, Midland, MI (US)

( * ) Notice: Subject to any disclaimer, the term of this patent is extended or adjusted under 35 U.S.C. 154(b) by 974 days.

This patent is subject to a terminal disclaimer.

(21) Appl. No.: 16/955,847

(22) PCT Filed: Dec. 17, 2018

(86) PCT No.: PCT/US2018/065950
§ 371 (c)(1),
(2) Date: Jun. 19, 2020

(87) PCT Pub. No.: WO2019/126010
PCT Pub. Date: Jun. 27, 2019

(65) Prior Publication Data
US 2020/0337981 A1    Oct. 29, 2020

Related U.S. Application Data

(60) Provisional application No. 62/608,598, filed on Dec. 21, 2017.

(51) Int. Cl.
| | | |
|---|---|---|
| *A61K 8/891* | (2006.01) | |
| *A61K 8/06* | (2006.01) | |
| *A61Q 5/02* | (2006.01) | |
| *A61Q 5/12* | (2006.01) | |

(52) U.S. Cl.
CPC ............. *A61K 8/891* (2013.01); *A61K 8/06* (2013.01); *A61Q 5/02* (2013.01); *A61Q 5/12* (2013.01)

(58) Field of Classification Search
CPC ... C11D 3/373; C11D 3/0015; C11D 11/0017; C11D 17/0017; A61K 8/891; A61K 8/06; A61Q 5/02; A61Q 5/12; A61Q 5/00; A61Q 5/06; A61Q 3/00; A61Q 3/02
See application file for complete search history.

(56) References Cited

U.S. PATENT DOCUMENTS

| | | |
|---|---|---|
| 4,247,442 A | 1/1981 | Shimizu |
| 4,831,070 A | 5/1989 | McInally et al. |
| 4,968,760 A | 11/1990 | Schiller et al. |
| 5,138,009 A | 8/1992 | Inoue |
| 5,223,495 A | 6/1993 | Inoue et al. |
| 6,545,104 B1 | 4/2003 | Mueller et al. |
| 7,740,664 B2 | 6/2010 | Benabdillah |
| 9,005,639 B2 | 4/2015 | Bekemeier et al. |
| 9,005,640 B2 | 4/2015 | Bekemeier et al. |
| 10,889,738 B2 | 1/2021 | Detemmerman et al. |
| 11,359,167 B2 * | 6/2022 | Dimitrova .......... C11D 17/0017 |
| 11,512,237 B2 * | 11/2022 | Detemmerman ...... C08G 77/26 |
| 2002/0120057 A1 | 8/2002 | Gosselink et al. |
| 2003/0065086 A1 | 4/2003 | Kosal |
| 2004/0058845 A1 | 3/2004 | Metrot et al. |
| 2005/0048124 A1 | 3/2005 | Sarangapani |
| 2005/0288415 A1 | 12/2005 | Beers et al. |
| 2007/0173596 A1 | 7/2007 | Landon et al. |
| 2007/0212314 A1 | 9/2007 | Murphy et al. |
| 2008/0295960 A1 | 12/2008 | Schalau, II et al. |
| 2008/0311396 A1 | 12/2008 | Hamada et al. |
| 2009/0004123 A1 | 1/2009 | Manuszak et al. |
| 2010/0069531 A1 | 3/2010 | Sakamoto et al. |
| 2010/0234517 A1 | 9/2010 | Plantenberg et al. |
| 2011/0311723 A1 | 12/2011 | Bekemeier et al. |
| 2012/0109036 A1 | 5/2012 | Sambasivam et al. |
| 2013/0338289 A1 | 12/2013 | Jadot et al. |
| 2014/0127140 A1 | 5/2014 | Ferritto et al. |
| 2014/0220843 A1 | 8/2014 | Liu et al. |
| 2014/0350176 A1 | 11/2014 | Fisher et al. |
| 2018/0215877 A1 | 8/2018 | Hori et al. |
| 2019/0192387 A1 | 6/2019 | Hori et al. |
| 2020/0063009 A1 | 2/2020 | Detemmerman et al. |
| 2020/0339915 A1 | 10/2020 | Dimitrova et al. |

FOREIGN PATENT DOCUMENTS

| | | |
|---|---|---|
| CN | 1914281 A | 2/2007 |
| CN | 103403075 A | 11/2013 |
| CN | 104559910 A | 4/2015 |

(Continued)

OTHER PUBLICATIONS

International Search Report for PCT/US2018/065950 dated Mar. 22, 2019, 4 pages.
Machine assisted English translation of CN1914281A obtained from https://patents.google.com/patent on Mar. 25, 2021, 27 pages.
Machine assisted English translation of CN104559910A obtained from https://patents.google.com/patent on Mar. 25, 2021, 5 pages.
Machine assisted English translation of CN104710960A obtained from https://patents.google.com/patent on Mar. 25, 2021, 7 pages.
Machine assisted English translation of CN104774587A obtained from https://patents.google.com/patent on Mar. 25, 2021, 7 pages.
Machine assisted English translation of JPS5676452A obtained from https://worldwide.espacenet.com/patent on Oct. 18, 2021, 5 pages.
Machine assisted English translation of JPS5676453A obtained from https://worldwide.espacenet.com/patent on Jul. 23, 2020, 5 pages.

(Continued)

*Primary Examiner* — Anna R Falkowitz
(74) *Attorney, Agent, or Firm* — Warner Norcross + Judd LLP

(57) ABSTRACT

The present disclosure relates to cosmetic compositions comprising an uncured silicone based polymer. In particular, the present disclosure relates to cosmetic compositions comprising an uncured silicone based polymer; and at least one cosmetic ingredient, optionally in a cosmetically acceptable medium. The present disclosure also relates to preparation methods and uses of the cosmetic compositions.

14 Claims, No Drawings

(56) References Cited

FOREIGN PATENT DOCUMENTS

| | | |
|---|---|---|
| CN | 104710960 A | 6/2015 |
| CN | 104736138 A | 6/2015 |
| CN | 104774587 A | 7/2015 |
| EP | 0315333 A2 | 5/1989 |
| EP | 0425121 A2 | 5/1991 |
| EP | 0802233 A2 | 10/1997 |
| GB | 2518468 A | 3/2015 |
| JP | S5676452 A | 6/1981 |
| JP | S5676453 A | 6/1981 |
| JP | 2008069869 A | 3/2008 |
| WO | 2000024851 A2 | 5/2000 |
| WO | 2000024856 A1 | 5/2000 |
| WO | 2000024858 A1 | 5/2000 |
| WO | 2003002809 A1 | 1/2003 |
| WO | 2005021058 A2 | 3/2005 |
| WO | 2008039654 A2 | 4/2008 |
| WO | 2011051236 A2 | 5/2011 |
| WO | 2012119940 A1 | 9/2012 |
| WO | 2015082877 A1 | 6/2015 |
| WO | 2016008022 A1 | 1/2016 |
| WO | 2017018358 A1 | 2/2017 |
| WO | WO2017018358 A1 | 2/2017 |
| WO | 2017085296 A1 | 5/2017 |
| WO | WO 2017/085296 * | 5/2017 ............... A61K 8/89 |
| WO | WO-2017085296 A1 * | 5/2017 ........... A61K 8/0208 |
| WO | 2017221940 A1 | 12/2017 |
| WO | WO2017221940 A1 | 12/2017 |
| WO | 2019126010 A1 | 6/2019 |

OTHER PUBLICATIONS

Machine assisted English translation of JP2008069869A obtained from https://patents.google.com/patent on Mar. 25, 2021, 6 pages.

N.J. Mills, "The Rheological Properties and Molecular Weight Distribution of Polydimethylsiloxane", European Polymer Journal, 1969, vol. 5, pp. 675-695.

Chen, Wei-Fu et al., "Covalently Cross-Linked Perfluorosulfonated Membranes with Polysiloxane Framework", Macromolecules 2007, vol. 40, No. 6, pp. 1987-1994.

Zhongzhan, Sun et al., "Synthesis and characterization of a new-type Schiff base side-chain polysiloxan[e] liquid crystal containing sulfonate groups", New Chemical Materials 2011, vol. 39, No. 5, pp. 56-58 (with English Abstract).

International Search Report for PCT/EP2016/078206 dated Jan. 26, 2017, 4 pages.

International Search Report for PCT/US2018/065956 dated Apr. 3, 2019, 4 pages.

* cited by examiner

COSMETIC COMPOSITION COMPRISING SILICONE MATERIALS

CROSS-REFERENCE TO RELATED APPLICATIONS

This application is the National Stage of International Appl. No. PCT/US2018/065950 filed on 17 Dec. 2018, which claims priority to and all advantages of U.S. Appl. No. 62/608,598 filed on 21 Dec. 2017, the content of which is hereby incorporated by reference.

TECHNICAL FIELD

This disclosure relates to cosmetic compositions comprising uncured silicone based polymers, and at least one cosmetic ingredient, in a cosmetically acceptable medium. Also disclosed is a process to prepare the cosmetic compositions and their uses in the care of keratinous substrates.

BACKGROUND

Cosmetic compositions include those compositions which are intended to be placed in contact with the external parts of the human body e.g. skin (epidermis), hair system, nails, mucosa, etc., (hereafter referred to as "keratinous substrates") with a view exclusively or mainly to clean, perfume, change appearance, protect keep in good condition or correct body odours of the human body. In some instances, cosmetic compositions may also include health care ingredients.

Silicone materials of various kinds may be used in cosmetic applications for sensory benefits, conditioning benefits or in some instance, as rheology modifiers. These silicone materials vary in their polymeric structure, in their viscosity or consistency, and in a lot of general properties such as hardness, flowability, stickiness, compatibility.

There is an ongoing need for silicone materials which are useful in the care of keratinous substrates and improved aesthetics in cosmetic applications. There is for example a continuing need for hair care compositions that give hair shiny appearance without an oily feel and look. In addition, there is a need for cosmetic compositions with good in-use experience, that look and feel better, and are more stable over time in terms of phase separation and aggregation. There is further a need for cosmetic compositions which provide improved coverage and hiding of wrinkles, fine lines, and pores, with improved moisturizing effect, while also providing a smooth, light feeling to the skin.

SUMMARY OF INVENTION

The present disclosure relates to cosmetic compositions comprising uncured silicone based polymers. In particular, the present disclosure relates to a cosmetic composition comprising an uncured silicone based polymer; and at least one cosmetic ingredient, in a cosmetically acceptable medium; where the uncured silicone based polymer is linear or branched, having the formula

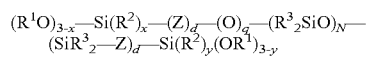

In which:
x is 0 (zero) or 1;
y is 0, 1, 2, or 3;
N is from 300 to 10,000;
d is 0 or 1, q is 0 or 1, and d+q=1; $R^1$, $R^2$ and $R^3$ are each independently linear alkyl groups containing 1 to 10 carbons; and
each Z is independently either
  (i) a linear or branched alkylene group having from 1 to 12 carbon atoms which may be interrupted by one or more linear or branched siloxane groups comprising from 1 to 20 silicon atoms; or
  (ii) an organic chain based on polyoxyalkylene based units which may be interrupted by one or more linear or branched siloxane groups comprising from 1 to 20 silicon atoms.

DESCRIPTION OF EMBODIMENTS

For the purpose of this invention "cosmetically acceptable compositions" include those compositions which are intended to be placed in contact with external parts of the human body, i.e. the aforementioned keratinous substrates, for exclusively or mainly cleaning, perfuming, changing appearance, protecting, keeping in good condition or correcting body odors.

The composition may be used in cosmetic applications, where they provide for one or more benefits like conditioning, hold, pleasant feel when used in a hair-care products like shampoo, conditioners, styling products; smooth and/or pleasant skin feel when present in a skin care cream; sun protection factor (SPF) booster when present in a sun care cream.

The terms "silanol", "hydroxysilyl", "hydroxyl", "SiOH" may be used interchangeably in the scope of the present invention, to indicate a condensation curable silyl terminating group of a polymer, bearing at least one hydroxyl functional group.

The terms "alkoxy", "hydrolysable", "SiOR" may be used interchangeably in the scope of the present invention, to indicate a condensation curable silyl terminating group of a polymer, bearing at least one hydrolysable functional group.

The relationship of molecular weight to viscosity of polydimethylsiloxane is described in scientific literature, for example, in at least Mills, E., European Polymer Journal, 1969, vol. 5, p. 675-695. The formula published in this article can be used to calculate approximately the weight average molecular weight of polymers (Mw) with an accuracy of about 10%. Polydispersity index (PI) is Mw/Mn, and from this relationship, the number average molecular weight (Mn) can be calculated.

The Mn and Mw of a silicone polymer are usually/often determined by gel permeation chromatography (GPC). This technique is a standard technique, and yields values for Mw (weight average), Mn (number average) and polydispersity index (PI) (where PI=Mw/Mn).

Mn values provided in this application have been determined by GPC and represent a typical value of the polymer used. If not provided by GPC, the Mn may also be obtained from calculation based on the dynamic viscosity of said polymer.

The uncured silicone based polymer as hereinbefore described is linear or branched, having the formula

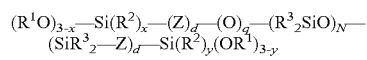

In which:
x is 0 (zero) or 1;
y is 0, 1, 2, or 3;
N is from 300 to 10,000;

d is 0 or 1 q is 0 or 1 and d+q=1; $R^1$, $R^2$ and $R^3$ are each independently linear alkyl groups containing 1 to 10 carbons; and each Z is independently either
  (i) a linear or branched alkylene group having from 1 to 12 carbon atoms which may be interrupted by one or more linear or branched siloxane groups comprising from 1 to 20 silicon atoms; or
  (ii) an organic chain based on polyoxyalkylene based units which may be interrupted by one or more linear or branched siloxane groups comprising from 1 to 20 silicon atoms.

Whilst x may be 0 or 1, it is preferred for x to be 0. Whilst y may be 0, 1, 2 or 3, it is preferred that y is 0 or 3 or a mixture of 0 and 3. N is from 300 to 10,000, alternatively from 300 and 1000, alternatively from 500 to 1000, alternatively from 600 to 900. $R^1$, $R^2$ and $R^3$ are independently linear alkyl groups containing 1 to 10 carbons, alternatively from 1 to 3 carbons, alternatively methyl or ethyl. In one embodiment $R^1$=methyl or ethyl, $R^2$=methyl and/or $R^3$=methyl. Blends of polymers having different values of x, y and N are included herein, in particular blends where x is 0 and y is 0 and/or 3.

In the case of both Z (i) or (ii) the polymer chains may be interrupted by one or more linear or branched siloxane groups comprising from 1 to 20 silicon atoms), if present the linear or branched siloxane groups will be made up of units of the structure —[$R^5_a$SiO$_{(4-a)/2}$]— where a can be from 2 to 4 and $R^5$ is either a saturated alkyl, phenyl or alkoxysilyl fragment of the type —(C$_b$H$_{2b}$)$_e$—Si—(R$^2$)$_v$(OR$^1$)$_{3-v}$, where b is from 1 to 10, e is zero or 1 and v is 0, 1 or 2. In such units typically a=2 resulting in a linear group of siloxane units. However, branching occurs when in one or more units a is zero or 1.

In the case of both options of Z (hereafter referred to as Z(i) and Z(ii) respectively) the polymer chains may be interrupted by one or more linear or branched siloxane groups comprising from 1 to 20 silicon atoms), if present the linear or branched siloxane groups will be made up of units of the structure —[$R^5_a$SiO$_{(4-a)/2}$]— where a can be from 2 to 4 and $R^5$ is either a saturated alkyl, phenyl or alkoxysilyl fragment of the type —(C$_b$H$_{2b}$)$_e$—Si—(R$^2$)$_v$(OR$^1$)$_{3-v}$, where b is from 1 to 10, e is zero or 1 and v is 0, 1 or 2. In such units typically a=2 resulting in a linear group of siloxane units. However, branching occurs when in one or more units a is zero or 1.

In one alternative of Z(i), Z(i) contains no linear or branched siloxane groups, i.e. Z(i) is a linear or branched alkylene group having from 1 to 12 carbon atoms, alternatively Z(i) is a linear or branched alkylene group having from 1 to 6 carbon atoms, Z(i) is a linear alkylene group having from 1 to 6 carbon atoms, alternatively Z(i) is a linear or branched alkylene group having from 2 to 4 carbon atoms.

When Z is type (ii), Z(ii) may be an organic chain based on polyoxyalkylene based units such polyoxyalkylene units preferably comprise a linear predominantly oxyalkylene polymer comprised of recurring oxyalkylene units, (—C$_n$H$_{2n}$—O—) illustrated by the average formula (—C$_n$H$_{2n}$—O—)$_m$ wherein n is an integer from 2 to 4 inclusive and m is an integer of at least four. The number average molecular weight of each polyoxyalkylene polymer block may range from about 300 to about 10,000, but can be higher in number average Mn-molecular weight. Moreover, the oxyalkylene units are not necessarily identical throughout the polyoxyalkylene monomer, but can differ from unit to unit. A polyoxyalkylene block, for example, can be comprised of oxyethylene units, (—C$_2$H$_4$—O—); oxypropylene units (—C$_3$H$_6$—O—); or oxybutylene units, (—C$_4$H$_8$—O—); or mixtures thereof. No particular tactility and/or blockiness of the polyglycol fragments is implied.

In one alternative Z(ii) contains no linear or branched siloxane groups, i.e. Z(ii) is a linear predominantly oxyalkylene polymer comprised of recurring oxyalkylene units. In Z(ii) there may be provided one of more alkylene groups having from 2 to 6 carbon atoms.

The uncured silicone based polymer as hereinbefore described may be provided in presence of an extender. When used the extender may be added before, after or during the preparation of the polymer, However it does not contribute to or participate in the polymerisation process. For ease of handling, a diluent may be added before the polymerisation reaction is initiated. Extenders as described herein are provided to dilute the polymer and prevent it from becoming too viscous during processing, i.e. further use.

Examples of extenders include
  (i) silicon containing liquids such as hexamethyldisiloxane, octamethyltrisiloxane, and other short chain linear siloxanes such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes such as hexamethylcyclotrisiloxane, octamethylcyclotetrasiloxane, decamethylcyclopentasiloxane, dodecamethylcyclohexasiloxane; further polydiorganosiloxanes, optionally including aryl functional siloxanes, having a viscosity of from 500 to 12,500 mPa·s, measured at 25° C.; using Brookfield cone plate viscometer RV DIII using a cone plate CP-52 at 5 rpm;
  (ii) Organic liquids such as butyl acetate, alkanes, alcohols, ketones, esters, ethers, glycols, glycol ethers, hydrocarbons, hydrofluorocarbons or any other material which can dilute the composition without adversely affecting any of the component materials. Hydrocarbons include isododecane, isohexadecane, Isopar L (C11-C 13), Isopar H (C11-C12), hydrogenated polydecene, mineral oil, especially hydrogenated mineral oil or white oil, liquid polyisobutene, isoparaffinic oil or petroleum jelly. Ethers and esters include isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols. A mixture of diluents may also be used.

The weight ratio of uncured silicone based polymer to extender/diluent can for example be 100/0 to 10/90, alternatively 70/30 to 20/80.

The composition as hereinbefore described additionally comprises one or more cosmetic ingredients. Cosmetic ingredients are those ingredients known to be used in cosmetic application. A wide review of such ingredients may be found in the CTFA cosmetic ingredient handbook.

Cosmetic ingredients include emollients, waxes, moisturizers, surface active materials such as surfactants or detergents or emulsifiers, thickeners, water phase stabilizing agents, pH controlling agents, preservatives and cosmetic biocides, sebum absorbents or sebum control agents, vegetable or botanical extracts, vitamins, proteins or amino-acids and their derivatives, pigments, colorants, fillers, silicone conditioning agents, cationic conditioning agents, hydrophobic conditioning agents, UV absorbers, sunscreen agents, antidandruff agents, antiperspirant agents, deodorant agents, skin protectants, hair dyes, nail care ingredients, fragrances or perfume, antioxidants, oxidizing agents, reducing agents, propellant gases, film formers and mixtures thereof.

Additional ingredients that may be used in the cosmetic compositions include fatty alcohols, colour care additives, anticellulites, pearlising agents, chelating agents, styling agents, ceramides, suspending agents and others.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as C30-45 Alkyl Methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa decane; branched C8-C16 esters; isohexyl neopentanoate; ester oils such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Example of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters and/or C30-45 alkyldimethylsilyl polypropylsilsesquioxane), and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic or non-ionic, and include organomodified silicones such as dimethicone copolyol; oxyethylenated and/or oxypropylenated ethers of glycerol; oxyethylenated and/or oxypropylenated ethers of fatty alcohols such as ceteareth-30, C12-15 pareth-7; fatty acid esters of polyethylene glycol such as PEG-50 stearate, PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof. The surface active materials may be the same or different from the surfactants used for emulsification, as discussed above.

Examples of non-ionic surfactants include polyoxyethylene alkyl ethers, polyoxyethylene fatty alcohols, polyoxyethylene alkylphenol ethers, polyoxyethylene lauryl ethers such as polyoxyethylene (23) lauryl ether, polyoxyethylene (4) lauryl ether, straight-chain, alkoxylated alcohols including primary alcohol alkoxylates, straight-chain secondary alcohol alkoxylates, alkyl phenol alkoxylates, olefinic alkoxylates, branched chain alkoxylates, specific examples including ethoxylated alcohols such as ethoxylated trimethylnonanol, C12-C14 secondary alcohol ethoxylates, ethoxylated, C10-Guerbet alcohol, ethoxylated, iso-C13 alcohol; poly(oxyethylene)-poly(oxypropylene)-poly(oxyethylene) tri-block copolymer (also referred to as poloxamers); tetrafunctional poly(oxyethylene)-poly(oxypropylene) block copolymer derived from the sequential addition of propylene oxide and ethylene oxide to ethylene diamine (also referred to as poloxamines), silicone polyethers, and mixtures thereof. Further examples of non-ionic surfactants include polyoxyethylene sorbitan monoleates, polyoxyethylene alkyl esters, polyoxyethylene sorbitan alkyl esters, polyethylene glycol, polypropylene glycol, diethylene glycol, polyoxyalkylene-substituted silicones (rake or ABn types), silicone alkanolamides, silicone esters, silicone glycosides, and mixtures thereof.

Further examples of non-ionic surfactants include dimethicone copolyols, fatty acid esters of polyols, for instance sorbitol or glyceryl mono-, di-, tri- or sesquioleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers, condensates of ethylene oxide with long chain fatty alcohols or fatty acids such as a C12-16 alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, and mixtures thereof.

Examples of cationic surfactants include alkylamine salts, quaternary ammonium salts, sulphonium salts, and phosphonium salts.

Examples of anionic surfactants include carboxylates (sodium 2-(2-hydroxyalkyloxy)acetate)), amino acid derivatives (N-acylglutamates, N-acylgly-cinates or acylsarcosinates), alkyl sulphsulphates, alkyl ether sulphsulphates and oxyethylenated derivatives thereof, sulphsulphonates, isethionates and N-acylisethionates, taurates and N-acyl N-methyltaurates, sulphsulphosuccinates, alkylsulphsulphoacetates, phosphates and alkyl phosphates, polypeptides, anionic derivatives of alkyl polyglycoside (acyl-D-galactoside uronate), and fatty acid soaps, and mixtures thereof, alkali metal, amine, or ammonium salts of higher fatty acids, alkylaryl sulphonates such as sodium dodecyl benzene sulphsulphonate, long chain fatty alcohol sulphsulphates, olefin sulphsulphates and olefin sulphsulphonates, sulphsulphated monoglycerides, sulphsulphated esters, sulphsulphonated ethoxylated alcohols, sulphsulphosuccinates, alkane sulphsulphonates, phosphate esters, alkyl isethionates, alkyl taurates, alkyl sarcosinates, and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, imidazoline compounds, alkylaminoacid salts, and mixtures thereof.

Examples of thickeners include acrylamide polymers and copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, hectorite and hectorite derivatives, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulphate salts of sodium, potassium, calcium and magnesium, as well as aluminium chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, and mixtures thereof.

Examples of sebum absorbents or sebum control agents include silica silylate, silica dimethyl silylate, dimethicone/vinyl dimethicone crosspolymer, polymethyl methacrylate, cross-linked methylmethacrylate, aluminium starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, *Ginkgo biloba*, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon or palm. Examples of herbal extracts include dill, horseradish, oats, neem, beet, broccoli, tea, pumpkin, soybean, barley, walnut, flax, *ginseng*, poppy, avocado, pea, sesame, and mixtures thereof.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate (vitamin A palmitate), retinyl acetate (vitamin A acetate), retinyl linoleate (vitamin A linoleate), and retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolysed form and they may also be quaternized, such as hydrolysed elastin, hydrolysed wheat powder, hydrolysed silk. Examples of protein include enzymes such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of cosmetic fillers include talc, micas, kaolin, zinc or titanium oxides, calcium or magnesium carbonates, silica, silica silylate, titanium dioxide, glass or ceramic beads, polymethylmethacrylate beads, boron nitride, aluminium starch octenylsuccinate, bentonite, magnesium aluminium silicate, nylon, silk powder metal soaps derived from carboxylic acids having 8-22 carbon atoms, non-expanded synthetic polymer powders, expanded powders and powders from natural organic compounds, such as cereal starches, which may or may not be crosslinked, copolymer microspheres, polytrap, silicone resin microbeads, and mixtures thereof. The fillers may be surface treated to modify affinity or compatibility with other ingredients, if appropriate.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate 0, phenylbenzimidazole sulphonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolysed collagen sulphonamide, benzylidene camphor sulphonic Acid, benzyl salicylate, bornelone, bumetriozole, butyl Methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulphonate, disodium distyrylbiphenyl triaminotriazine stilbenedisulphonate, disodium distyrylbiphenyl disulphonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulphonic acid, polyacrylamidomethyl benzylidene camphor, potassium methoxycinnamate, potassium phenylbenzimidazole sulphonate, red petrolatum, sodium phenylbenzimidazole sulphonate, sodium urocanate, TEA-phenylbenzimidazole sulphonate, TEA-salicylate, terephthalylidene dicamphor sulphonic acid, titanium dioxide, tri-PABA panthenol, urocanic acid, VA/crotonates/methacryloxybenzophenone-1 copolymer, and mixtures thereof.

Examples of antidandruff agents include pyridinethione salts, selenium compounds such as selenium disulphide, and soluble antidandruff agents, and mixtures thereof.

Examples of antiperspirant agents and deodorant agents include aluminium chloride, aluminium zirconium tetrachlorohydrex GLY, aluminium zirconium tetrachlorohydrex PEG, aluminium chlorohydrex, aluminium zirconium tetrachlorohydrex PG, aluminium chlorohydrex PEG, aluminium zirconium trichlorohydrate, aluminium chlorohydrex PG, aluminium zirconium trichlorohydrex GLY, hexachlorophene, benzalkonium chloride, aluminium sesquichlorohydrate, sodium bicarbonate, aluminium sesquichlorohydrex PEG, chlorophyllin-copper complex, triclosan, aluminium zirconium octachlorohydrate, zinc ricinoleate, and mixtures thereof.

Examples of skin protectants include allantoin, aluminium acetate, aluminium hydroxide, aluminium sulphate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulphate; 2-amino-4-hydroxyethylaminoanisole; 2-amino-4-hydroxyethylaminoanisole sulphate; 2-amino-5-nitrophenol; 4-amino-2-nitrophenol; 4-amino-3-nitrophenol; 2-amino-4-nitrophenol sulphate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulphate; 2,3-diaminodihydropyrazolo pyrazolone dimethosulphonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulphate; direct dyes; 4-ethoxy-m-phenylenediamine sulphate; 3-ethylamino-p-cresol sulphate; N-ethyl-3-nitro PABA; gluconamidopropyl aminopropyl dimethicone; Haematoxylon brasiletto wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulphate; 2-hydroxyethyl picramic acid; hydroxypyridinone; hydroxysuccinimidyl C21-22 isoalkyl acidate; isatin; *Isatis tinctoria* leaf powder; 2-methoxymethyl-p-phenylenediamine sulphate; 2-methoxy-p-phenylenediamine sulphate; 6-methoxy-2,3-pyridinediamine HCl; 4-methylbenzyl 4,5-diamino pyrazole sulphate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine;

4-nitro-m-phenylenediamine sulphate; 4-nitro-o-phenylenediamine sulphate; 2-nitro-p-phenylenediamine sulphate; 6-nitro-2,5-pyridinediamine; 6-nitro-o-toluidine; PEG-3 2,2'-di-p-phenylenediamine; p-phenylenediamine HCl; p-phenylenediamine sulphate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulphanilate; solvent yellow 85; solvent yellow 172; tetraaminopyrimidine sulphate; tetrabromophenol blue; 2,5,6-triamino-4-pyrimidinol sulphsulphate and 1,2,4-trihydroxybenzene.

Example of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; *Cetraria islandica* extract; *Chondrus crispus*; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* Oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulphate, disodium rutinyl disulphate, distearyl thiodipropionate, ditridecyl thiodipropionate, dodecyl gallate, ethyl ferulate, ferulic acid, hydroquinone, hydroxylamine HCl, hydroxylamine sulphate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulphite, propyl gallate, rosmarinic acid, rutin, sodium ascorbate, sodium ascorbyl/cholesteryl phosphate, sodium bisulphite, sodium erythorbate, sodium metabisulphide, sodium sulphite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulphate, calcium peroxide, hydrogen peroxide, magnesium peroxide, melamine peroxide, potassium bromate, potassium caroate, potassium chlorate, potassium persulphate, sodium bromate, sodium carbonate peroxide, sodium chlorate, sodium iodate, sodium perborate, sodium persulphate, strontium dioxide, strontium peroxide, urea peroxide, zinc peroxide, and mixtures thereof.

Examples of reducing agents are ammonium bisufite, ammonium sulphite, ammonium thioglycolate, ammonium thiolactate, cystemaine HCl, cystein, cysteine HCl, ethanolamine thioglycolate, glutathione, glyceryl thioglycolate, glyceryl thioprorionate, hydroquinone, p-hydroxyanisole, isooctyl thioglycolate, magnesium thioglycolate, mercaptopropionic acid, potassium metabisulphite, potassium sulphite, potassium thioglycolate, sodium bisulphite, sodium hydrosulphite, sodium hydroxymethane sulphonate, sodium metabisulphite, sodium sulphite, sodium thioglycolate, strontium thioglycolate, superoxide dismutase, thioglycerin, thioglycolic acid, thiolactic acid, thiosalicylic acid, zinc formaldehyde sulphoxylate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

Examples of film formers include those polymers capable, by themselves or in the presence of an auxiliary filmforming agent, of forming a macroscopically continuous film on a support, especially on keratin materials, preferably a cohesive film and better still a film whose cohesion and mechanical properties are such that the said film can be isolated from the said support.

Where appropriate, i.e. dependent on end use, health care ingredients may be used in cosmetic compositions. Healthcare ingredients which may be included herein include but are not restricted to anti-acne agents, antibacterial agents, antifungal agents, skin bleaching agents, skin and scalp soothing agents, antiseptic agents, antibacterial agents and/or anti-inflammatory agents.

Examples of anti-acne agents include salicylic acid, sulphur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of external analgesics are benzyl alcohol, *capsicum* oleoresin (*Capsicum frutescens* oleoresin), methyl salicylate, camphor, phenol, capsaicin, juniper tar (*Juniperus* oxycedrus tar), phenolate sodium (sodium phenoxide), *capsicum* (*Capsicum frutescens*), menthol, resorcinol, methyl nicotinate, turpentine oil (turpentine), and mixtures thereof.

An example of a skin bleaching agent is hydroquinone.

The general level of uncured silicone based polymer in the cosmetic compositions may vary from 0.1% to 80% by weight, alternatively from 0.1% to 10%, alternatively from 0.5% to 5%, relative to the total weight of the cosmetic composition. The cosmetic ingredient is present at a level of from 0.01% to 99.99% by weight, relative to the total weight of the cosmetic composition. The cosmetic ingredient may be a mixture of cosmetic ingredients as listed above.

In some instances, the uncured silicone based polymer is used in conjunction with a cosmetic ingredient selected from a cationic conditioning agent, a hydrophobic conditioning agent, or mixtures thereof, in a cosmetically acceptable medium.

The cosmetically acceptable medium as hereinbefore described may include but are not limited to water, solvents, and/or mixtures and emulsions thereof. Solvents include low molecular weight organic solvents that are highly soluble in water, e.g., C1-C4 monohydric alcohols, C2-05 polyhydric alcohols including alkylene glycols, polyalkylene glycols, alkylene carbonates, and mixtures thereof. Typical solvents include ethanol, propanol, isopropanol, n-butyl alcohol, t-butyl alcohol, ethylene glycol, diethylene glycol, propylene glycol, dipropylene glycol, glycerol, propylene carbonate, and mixtures thereof. Other suitable examples of cosmetically acceptable carriers include short chain polysiloxanes having a viscosity below 10 mPa·s, alternatively below 5 mPa·s, alternatively below 3 mPa·s, Cyclic polysiloxanes comprising 3 to 12 silicon atoms, alternatively comprising 4 to 7 silicon atoms, alternatively 4 to 6 silicon atoms, or blends thereof, organic mineral oils, organic polyesters and suitable blends of any of the above. The viscosity of these materials can be measured at 25° C. using any method known in the art as for example Wells/Brookfield™ Cone & Plate devices DV3TLVCP or DV2TLVCP or DV1MLVCP, equipped with cone-plate spindles suitable foe low viscosity as for example CPA-40Z, CPA-41Z, CPA-42Z. Details and ranges are available from www.brookfieldengineering.com.

The uncured silicone based polymer described herein may be introduced into a cosmetic composition, as also described herein, in any acceptable form. For example, it may be provided neat (undiluted), in a diluted form e.g. with extender as previously discussed or in an emulsion form, which may be prepared by any known method, e.g. by the methods as discussed below.

The present disclosure further provides a process for preparing an emulsion by:
I) forming a mixture comprising;
  A) 100 parts by weight of uncured silicone based polymer as hereinbefore described,
  B) 0.1 to 50 parts by weight of a surfactant,
II) admixing a sufficient amount of water to the mixture from step (I) to form an emulsion, having a continuous phase and a dispersed phase,
III) optionally, further shear mixing the emulsion and/or diluting of the emulsion with the continuous phase.

The amount of surfactant (which, as indicated above, is a suitable cosmetic ingredient) added in step I should be 0.1 to 50 parts by weight, alternatively 1 to 50 parts by weight, alternatively 2 to 20 parts by weight, for every 100 parts by weight of uncured silicone based polymer. The surfactant may be an anionic surfactant, cationic surfactant, nonionic surfactant, amphoteric surfactant, or a mixture thereof, with the surfactants being, for the sake of example any of those previously identified above.

Mixing in step (I) can be accomplished by any suitable method in the art to effect mixing of. The mixing may occur either as a batch, semi-continuous, or continuous process. Mixing may occur, for example using, batch mixing equipment with medium/low shear include change-can mixers, double-planetary mixers, conical-screw mixers, ribbon blenders, double-arm or sigma-blade mixers; batch equipment with high-shear and high-speed dispersers include those made by Charles Ross & Sons (NY), Hockmeyer Equipment Corp. (NJ); batch equipment with high shear actions include Banbury-type (CW Brabender Instruments Inc., NJ) and Henschel type (Henschel mixers America, TX); centrifugal force-based, high shear mixing devices as for example Speed Mixer® (Hauschild & Co KG, Germany). Illustrative examples of continuous mixers/compounders include extruders single-screw, twin-screw, and multi-screw extruders, co-rotating extruders, such as those manufactured by Krupp Werner & Pfleiderer Corp (Ramsey, NJ), and Leistritz (NJ); twin-screw counter-rotating extruders, two-stage extruders, twin-rotor continuous mixers, dynamic or static mixers or combinations of this equipment.

The temperature and pressure at which the mixing of step (I) occurs is not critical, but generally is conducted at ambient temperature (20-25° C.) and pressures. Typically, the temperature of the mixture will increase during the mixing process due to the mechanical energy associated when shearing such high viscosity materials.

Step (II) of the process involves admixing water to the product of step (I) to form an emulsion. Typically 5 to 2000 parts by weight of water are introduced per every 100 parts by weight of the product of product of step (I) to form an emulsion. The water is added to the product of step (I) at a suitable rate, with additional mixing, so as to form an emulsion with the product of step (I). While this amount of water can vary depending on the selection of the surfactants, generally the amount of water is from 0.1 to 2000 parts per 100 parts by weight of the product of step (I), alternatively from 5 to 500 parts per 100 parts by weight of the product of step 1, or alternatively from 5 to 100 parts per 100 parts by weight of the product of step (I).

The addition of water to the product of from step (I) may be done in incremental portions, whereby each incremental portion comprises less than 30 weight % of the mixture from step (I) and each incremental portion of water is added successively to the previous after the dispersion of the previous incremental portion of water, wherein sufficient incremental portions of water are added to form an emulsion with the uncured silicone based polymer.

Mixing in step (II) can be accomplished by any method known in the art to effect mixing of high viscosity materials. The mixing may occur either as a batch, semi-continuous, or continuous process. Any of the mixing methods as described for step (I), may be used to effect mixing in step (II). Alternatively, mixing in step (II) may also occur via those techniques known in the art to provide high shear mixing to effect formation of emulsions. Representative of such high shear mixing techniques include: homogenizers, sonolators, and other similar shear devices.

Optionally, the emulsion formed in step (II) may be further sheared according to step (III) to reduce particle size and/or improve long term storage stability. The shearing may occur by any of the mixing techniques discussed above. In some cases it might be necessary to run one or several of the steps (I) to (III) under lower pressure or vacuum.

The above method provide method for making the cosmetic composition in which the surfactant and diluent, when present are the cosmetic ingredients. However, the above may also be a partial preparation step as a means of introducing the silicone based polymer into other ingredients of a composition.

The cosmetic composition may be prepared by a process comprising the steps of
  i. Mixing uncured silicone based polymer as hereinbefore described ii. and at least one cosmetic ingredient,
iii. optionally in the presence of a cosmetically acceptable medium.

The uncured silicone based polymer may be provided in any suitable form, i.e. it may be in a "neat" or undiluted form, in an extended form (i.e. in a mixture with an extender as described above) or in the presence of a cosmetically acceptable medium, e.g. in an emulsion. The cosmetic composition may be prepared in the form of the emulsion when mixing the above ingredients together.

The emulsions of the present disclosure may be an oil/water emulsion, a water/oil emulsion, a multiple phase or triple emulsion. The emulsions may be prepared using the mixing apparatus described above.

In one embodiment, the emulsions of the present disclosure are oil/water emulsions. The present oil/water emulsions may be characterized by average volume particle of the dispersed (oil) phase in the continuous aqueous phase. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 0.5 is the particle size measured in volume corresponding to 50% of the cumulative particle population. In other words if Dv 0.5=10 µm, 50% of the particle have an average volume particle size below 10 µm and 50% of the particle have a volume average particle size above 10 µm. Unless indicated otherwise all average volume particle sizes are calculated using Dv 0.5.

The average volume particle size of the dispersed siloxane particles in the oil/water emulsions may vary between 0.1 µm and 150 µm; or between 0.1 µm and 30 µm; or between 0.2 µm and 5.0 µm.

In one embodiment of this invention the composition can be formulated as a serum. For the purpose of this invention "serum" is defined as a blend of the uncured silicone based polymer with at least one low viscosity cosmetically acceptable carrier, preferably a volatile one, e.g. one of the solvents as described above, and also containing at least one cosmetic ingredient.

The cosmetic compositions may be prepared by mixing the uncured silicone based polymer in the appropriate phase of a final cosmetic composition as hereinbefore described.

When the uncured silicone based polymer is used in its neat (undiluted) form, it may be added into a hydrophobic phase. The hydrophobic phase may be a single phase, that is, a monophasic system, or the hydrophobic phase in an anhydrous system. In some events, a second hydrophilic or aqueous phase may be mixed with the hydrophobic phase to provide for a dispersion or emulsion.

When the uncured silicone based polymer is used in emulsion form, it may be mixed with the aqueous phase ingredients and optionally subsequently mixed with an optional second hydrophobic phase. When there are multiple phases, the different phases may subsequently be mixed together, optionally under heating.

The process may be conducted at temperatures ranging of from 15 to 90° C., alternatively of from 20 to 60° C., alternatively at room temperature (25° C.), using simple propeller mixers, counter-rotating mixers, or homogenizing mixers. No special equipment or processing conditions are typically required. Depending on the type of composition prepared, the method of preparation will be different, but such methods are well known in the art.

The cosmetic compositions may be prepared with a carrier that permits application in any conventional form, e.g. in the form of liquids, rinses, lotions, creams, pastes, gels, foams, mousses, ointments, sprays, aerosols, soaps, sticks, soft solids, solid gels, and gels. The cosmetic compositions may be in the form of monophasic systems, biphasic or alternate multiphasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, nail care compositions and powders, medicament creams, pastes or sprays.

Skin care compositions include shower gels, soaps, hydrogels, creams, lotions and balms; antiperspirants; deodorants such as sticks, soft solid, roll on, aerosol, and pump sprays; skin creams; skin care lotions; moisturizers; facial treatments such as wrinkle control or diminishment treatments; exfoliates; body and facial cleansers; bath oils; perfumes; colognes; sachets; sunscreens; mousses; pre-shave and after-shave lotions; shaving soaps; shaving lathers; depilatories; make-ups; color cosmetics; foundations; concealers; blushes; lipsticks; eyeliners;

mascaras; oil removers; color cosmetic removers, powders, and kits thereof. Skin care compositions exclude patches.

Hair care compositions include shampoos, rinse-off conditioners, leave-in conditioners and styling aids, gels, sprays, pomades, mousses, waxes, cuticle coats, hair colorants, hair relaxants, hair straighteners, permanents, and kits thereof.

Nail care compositions include color coats, base coats, nail hardeners, and kits thereof.

The cosmetic compositions may be used by the standard methods, such as applying them to the human or animal body, e.g. skin or hair, using applicators, brushes, applying by hand, pouring them and/or possibly rubbing or massaging the composition onto or into the body. Removal methods, for example for colour cosmetics are also well known standard methods, including washing, wiping, scrubbing and the like.

The invention also comprises a method of treating keratinous substrates, such as hair, nails or skin, by applying a cosmetic composition as hereinbefore described to said keratinous substrates.

The cosmetic compositions may be used on hair in a conventional manner. An effective amount of the composition for washing or conditioning hair is applied to the hair. Such effective amounts generally range from about 1 g to about 50 g, preferably from about 1 g to about 20 g. Application to the hair typically includes working the cosmetic composition through the hair such that most or all of the hair is contacted with the cosmetic composition. These steps can be repeated as many times as desired to achieve the desired benefit.

Benefits obtained from using the cosmetic compositions on hair include one or more of the following benefits: hair conditioning, softness, detangling ease, silicone deposition, anti-static, anti-frizz, lubricity, shine, strengthening, viscosity, tactile, wet combing, dry combing, improvement in coloration process, color retention, straightening, heat protection, styling, or curl retention.

The cosmetic compositions may be used on skin in a conventional manner. An effective amount of the composition for the purpose is applied to the skin. Such effective amounts generally range from about 1 mg/cm$^2$ to about 3 mg/cm$^2$. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: skin softness, suppleness, moisturisation, skin feel, foam generation, durability, substantivity, long lasting, long wear, shine or mattifying effect, SPF boost, pollutants barrier.

The invention thus also comprises a process for the care of keratinous substrates, such as hair or skin, by applying a cosmetic composition as hereinbefore described to said keratinous substrates.

The process to care for keratinous substrates comprises the steps of
a. Providing for a cosmetic composition comprising uncured silicone based polymer and at least one cosmetic ingredient, optionally in a cosmetically acceptable medium,
b. Applying the composition to the keratinous substrate
c. Optionally rinsing.

The optional standing time of the process of caring or conditioning keratinous substrates e.g. hair fibres may range of from 10 seconds to 1 hour, alternatively of from 30 seconds to 30 minutes, alternatively of from 30 seconds to 10 minutes.

In one embodiment, the present invention provides for the use of the present cosmetic composition to care for keratinous substrates, that is to cleanse, to condition, to refresh, to make up, to remove make up, to fix hair and for nail care applications.

In yet another aspect the present emulsions can be used as part of colorant of fixative compositions and applied as pre-, during-, post-treatment in the process of coloring or perming hair. The purposes could range from color retention and color enhancement to again conditioning of the colored hair fibers.

Examples

The following examples are provided to demonstrate preferred embodiments of the invention. Unless otherwise indicated, all recipes are in parts by weight, and not %, therefore the sum is not necessarily 100.

Hair hydrophobization tests were undertaken with respect to:
(i) two examples in accordance with the present disclosure as hereinbefore described;
(ii) a reference material decamethylcyclopentasiloxane (hereafter referred to as "D5");
(iii) Six commercial products identified as comparatives 1 to 6; and
(iv) four condensation cured silicone based materials identified as Comparatives 7 to 10).

As indicated above Comparatives 7 to 10 are cured products which were pre-prepared from the following ingredients in the amounts provided in Table 1 below.

Following abbreviations are used in the table 1:
1) Polymer type 1 was an α,ω-Dimethylhydroxysilyl terminated polydimethyl siloxane with viscosity at 23° C. of 13,500 mPa·s (viscosity measured using a Brookfield cone plate viscometer RV DIII using a cone plate CP-52 at 5 rpm),)
2) Polymer type 2 was an α,ω-Dimethyl hydroxysilyl terminated polydimethyl siloxane with viscosity at 23° C. of 50,000 mPa·s (viscosity measured using a Brookfield cone plate viscometer RV DIII using a cone plate CP-52 at 0.55 rpm)
3) X-linker: $(EtO)_3$—Si—$C_2H_4$—$[SiO(CH_3)_2]_{(800-900)}$—$Si(CH_3)_2C_2H_4$—Si-$(EtO)_3$ having a viscosity at 23° C. of 50,000 mPa·s (viscosity measured using a Brookfield cone plate viscometer RV DIII using a cone plate CP-52 at 3 rpm)
4) TNBT=tetra n-butyl titanate, commercially available as Tyzor TNBT from Dorf Ketal
5) 200 fluid 2 mPa·s which is a commercial sample of trimethyl end-capped polydimethyl siloxane having a viscosity of 2 mPa·s at 23° C. commercially available from Dow Corning under the trade name Dow Corning® 200 fluid 2 cSt. Viscosity values were not otherwise measured on this product.

TABLE 1

| Reactant | Comp. 7 | Comp. 8 | Comp. 9 | Comp. 10 |
|---|---|---|---|---|
| X-linker E (parts by weight) | 30.0 | 15.0 | 30.0 | 40.0 |
| polymer type 1 (parts by weight) | 100.00 | 100.00 | | |
| polymer type 2 (parts by weight) | | | 200.00 | 200.00 |
| TNBT (parts by weight) | 0.25 | 0.25 | 0.30 | 0.25 |
| Dow Corning ® 200 fluid, 2 cSt (parts by weight) | 200.00 | 200.00 | 400.00 | 200.00 |

Typically 80-90 g of Comparatives 7 to 10 were prepared using the following protocol: the linear OH-terminated polydimethyl siloxane(s) was mixed with cross-linker and with the optional diluent (200 fluid, 2 mPa·s), using a speed mixer DAC 150.1 FV (available from Hauschield, Germany) at 3000 rpm for 30 s. The catalyst, tetra-n-butyl titanate (NBT), was then added into the resulting mixture which was subsequently stirred again for 90 seconds at maximum speed using the same device. The final resulting material for each of comparatives 7 to 10 was then left in an open container at ambient conditions for 3 weeks to allow for full cure. Dow Corning® 200 fluid 2 cSt is highly volatile given its low viscosity. When used as a diluent the volume lost through volatility was replaced on a daily basis. The resulting cured materials of Comparatives 7 to 10 were crystal clear polymers or gels.

The static contact angle of a drop of 30 of water deposited on the hair tress was measured using a Goniometer (Contact Angle CAM 200 from KSV Instruments Ltd.). At least 3 measurements per sample were done. The higher the contact angle value, the more hydrophobic (the better) the sample. Each value in table 2 is an average of all measurements performed in the particular case.

TABLE 2

| Samples | Silicone material | Diluent | Contact Angle on Hair (°) |
|---|---|---|---|
| Ex. 1 | Trimethoxy end-capped polydimethyl siloxane with viscosity of 50000 mPa · s (100% active) | D5 | 118 |
| Ex. 2 | $(EtO)_3$—Si—$C_2H_4$—$(SiO(CH_3)_2)_N$—$Si(CH_3)_2$—$C_2H_4$—Si—$(OEt)_3$ N = 800 +/− 10% (100% active) | D5 | 118 |
| Ref. 1 | Dow Corning ® 245 Fluid (100%: cyclopentasiloxane) | | 68 |
| Comp. 1 | Dow Corning ® 200 Fluid, 60,000 mPa · s (100%: dimethicone) | D5 | 100 |
| Comp. 2 | Dow Corning ® 8500 Conditioning Agent (100% Bis (C13-15 Alkoxy) PG Amodimethicone) | D5 | 111 |
| Comp. 3 | Dow Corning ® 2-8566 Amino Fluid (100% Amodimethicone) | D5 | 113 |
| Comp. 4 | Xiameter ® OFX-8800 Fluid (100% organosilicone premium hydrophilic softener) | D5 | 100 |
| Comp. 5 | Dow Corning ® FA 4003 DM Silicone Acrylate (100% Dimethicone (and) Acrylates/Polytrimethylsiloxymethacrylate Copolymer) | D5 | 108 |
| Comp. 6 | Dow Corning ® 3901 Liquid Satin Blend (Dimethicone (and) Dimethicone/Vinyl Dimethicone Crosspolymer) | 200 fluid | 85 |
| Comp. 7 | (See Table 1) | 200 fluid | 108 |
| Comp. 8 | (See Table 1) | 200 fluid | 106 |
| Comp. 9 | (See Table 1) | 200 fluid | 113 |
| Comp. 10 | (See Table 1) | 200 fluid | 118 |

The reference material and other comparative materials are listed under their respective Trade Names in Table 2 below. The details in parenthesis are INCI names (when available).

The Hair Hydrophobization test

A Contact Angle test is designed to evaluate hydrophobicity of hair fibers treated with products or formulations. Hair hydrophobicity is a very good indication of the damage of hair. Healthy, undamaged hair is typically hydrophobic. As soon as the hair is damaged, i.e. by chemical, mechanical, physical or environmental factors—it becomes more porous and hydrophilic.

Commercially available hair tresses (bleached Caucasian hair from International Hair Importers & Products (IHIP), 2 g/25 cm) were washed, dried and then 200 µl of 3% solution in Dow Corning® 245 Fluid (100%: cyclopentasiloxane, commonly abbreviated as D5 or 200 fluid, 2 mPa·s of each material in Table 2 were applied and manually spread on each tress. The tresses were combed twice and then left to dry overnight.

Typically it is understood that a material is defined as hydrophobic when its water contact angle value is above 90° and is defined as hydrophilic when it is below 90°. Hence, it is believed fair to categorise our results as follows:
  super-hydrophobic ≥150°
  very hydrophobic—values which >100° but <150°
  moderate hydrophobic values which are >90° but ≤100°
  moderate Hydrophilic values which are >60° but ≤90°
  very hydrophilic values which are ≥60°.

From Table 2 it can be seen that both Examples 1 and 2 provide:

Better hair fiber hydrophobization than the Reference (which also functions as the carrier (cyclopentasiloxane) or linear dimethicone;

Better hair fiber hydrophobization than silicone acrylates, dimethicone (and) dimethicone/vinyl dimethicone crosspolymer and acrylates/polytrimethylsiloxymethacrylate copolymer Similar or better hair fiber hydrophobization than the amino functional polysiloxanes;

Similar or better hair fiber hydrophobization than the silicone based material cured via a condensation cure chemistry.

The examples are more appropriate for use in these applications than amino functional silicones because the latter tend to have yellowing issues, high odor and can be a skin-irritant. Furthermore, the silicone polymer described herein and exemplified in Examples 1 and 2 can be used in aerosol formulations in contrast to many amino-modified siloxanes (e.g. amodimethicones).

Whilst the silicone based materials cured via condensation cure chemistry (comparative examples 7 to 10) gave good results, they are far more difficult to produce and cure compared to the polymers used herein not least because of the need for several ingredients to be mixed as well as the need to cure the resulting composition. Given we are solely using an uncured polymer much of this effort is negated.

Maintenance of the Hydrophobization Benefit after Multiple Washings

The results depicted in Table 3 show the maintenance of the hydrophobic benefit on the hair samples after multiple washes after being washed 15 times with a 9% solution of SLS (sodium lauryl sulphate) in distilled water and dried. The contact angle of the water on the washed tresses was measured in the same manner as described above.

TABLE 3

| Samples | Composition | Contact Angle on Hair (°) Initial | Contact Angle on Hair (°) after 15 washes |
|---|---|---|---|
| Ex. 2 | $(EtO)_3$—Si—$C_2H_4$—$(SiO(CH_3)_2)_N$—$Si(CH_3)_2$—$C_2H_4$—Si—$(OEt)_3$ | 118 | 50 |
| Ref. | N = 800 +/− 10% (100% active) | 68 | 0 |
| Comp. 1 | Dow Corning ® 245 Fluid (100%: cyclomethicone) | 100 | 0 |
| Comp. 5 | Dow corning ® 200 Fluid, 60,000 mPa · s (100%: dimethicone) | 108 | 50 |
| Comp. 6 | Dow Corning ® FA 4003 DM Silicone Acrylate (Dimethicone (and) Acrylates/Polytrimethylsiloxymethacrylate Copolymer) | 85 | 35 |

It can be seen that the examples herein gave improved long term results than the competing materials.

The invention claimed is:

1. A cosmetic composition comprising an uncured silicone based polymer; and at least one cosmetic ingredient, optionally in a cosmetically acceptable medium;
wherein the uncured silicone based polymer is linear or branched and has the general formula:

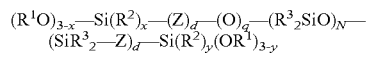
$(SiR^3{}_2$—$Z)_d$—$Si(R^2)_y(OR^1)_{3-y}$ where:
x is 0 or 1;
y is 0, 1, 2, or 3;
N is from 300 to 10,000;
d is 0 or 1, q is 0 or 1, and d+q=1;
$R^1$, $R^2$ and $R^3$ are each independently linear alkyl groups containing 1 to 10 carbons; and
each Z is independently either
(i) a linear or branched alkylene group having from 1 to 12 carbon atoms which may be interrupted by one or more linear or branched siloxane groups comprising from 1 to 20 silicon atoms; or
(ii) an organic chain based on polyoxyalkylene based units which may be interrupted by one or more linear or branched siloxane groups comprising from 1 to 20 silicon atoms;
wherein the cosmetic composition is in the form of a shampoo, a cream, a rinse-off conditioner, a leave-in conditioner, or a gel.

2. The cosmetic composition of claim 1, wherein y is 0, 3, or a mixture of 0 and 3.

3. The cosmetic composition of claim 1, wherein the uncured silicone based polymer is in neat form, in diluted form, or in emulsion form.

4. The cosmetic composition claim 1, wherein the cosmetic ingredient is selected from the group consisting of shampoo ingredients, hair conditioner ingredients, emollients, waxes, moisturizers, surface active materials, thickeners, water phase stabilizing agents, pH controlling agents, preservatives and cosmetic biocides, sebum absorbents, sebum control agents, vegetable extracts, botanical extracts, vitamins, proteins and their derivatives, amino-acids and their derivatives, pigments, colorants, fillers, silicone conditioning agents, cationic conditioning agents, UV absorbers, sunscreen agents, antidandruff agents, antiperspirant agents, deodorant agents, skin protectants, hair dyes, nail care ingredients, fragrances, perfume, antioxidants, oxidizing agents, reducing agents, film formers, propellant gases, fatty alcohols, color care additives, pearlising agents, chelating agents, film formers, styling agents, ceramides, suspending agents, and combinations thereof.

5. The cosmetic composition of claim 1, wherein the cosmetic ingredient is selected from the group consisting of hair care ingredients, nail care ingredients, and combinations thereof.

6. The cosmetic composition of claim 1, which is in the form of a cream, a gel, a free flowing powder, a pressed powder, a paste, a solid, a freely pourable liquid, or an aerosol.

7. A process for preparing an emulsion of the cosmetic composition in accordance with claim 1, said process comprising:
I) forming a mixture comprising;
A) 100 parts by weight of the uncured silicone based polymer,
B) 0.1 to 50 parts by weight of a surfactant; and
II) admixing a sufficient amount of water to the mixture from step I) to form an emulsion;
III) optionally, further shear mixing the emulsion and/or diluting of the emulsion with continuous phase.

8. A process for preparing the cosmetic composition in accordance with claim 1, said process comprising mixing the uncured silicone based polymer and the at least one cosmetic ingredient, optionally in the presence of the cosmetically acceptable medium.

9. The process of claim 8, wherein the cosmetic composition is prepared by mixing the uncured silicone based polymer in neat form with the ingredients of a hydrophobic phase, optionally under heating.

10. The process according to claim 8, wherein the cosmetic composition is prepared by mixing the uncured silicone based polymer in emulsion form with the ingredients of a hydrophilic phase, optionally under heating.

11. A process to care for keratinous substrates, said process comprising:
providing the cosmetic composition in accordance with claim 1; and
applying the cosmetic composition to the keratinous substrate;
optionally, rinsing the keratinous substrate.

12. The cosmetic composition of claim 1, wherein the cosmetically acceptable medium is present.

13. The process according to claim 11, wherein the keratinous substrates are hair, finger nails, and/or toe nails.

14. The cosmetic composition according to claim 1, which is in the form of a hair care composition or a nail care composition.

* * * * *